United States Patent [19]

Mulvey et al.

[11] 4,195,023

[45] Mar. 25, 1980

[54] 2-(2-FUROYL)1,2-BENZISOTHIAZOLE-3-ONE, 2-(2-FUROYL) SACCHARIN, AND 2-(2-THENOYL) SACCHARIN

[75] Inventors: Dennis Mulvey, Milford; Howard Jones, Holmdel; Morris Zimmerman, Watchung, all of N.J.

[73] Assignee: Merck & Co., Inc., Rahway, N.J.

[21] Appl. No.: 606,271

[22] Filed: Aug. 20, 1975

[51] Int. Cl.$^2$ .......................................... C07D 275/06
[52] U.S. Cl. .............................. 548/209; 260/347.3; 260/347.5; 260/544 S; 260/558 S; 260/559 T; 424/270; 560/18; 548/210; 546/270
[58] Field of Search ............................ 260/304 A, 301

[56] References Cited

FOREIGN PATENT DOCUMENTS 46-36613 10/1971 Japan ........................................ 260/301

OTHER PUBLICATIONS

Ramegowda et al, *Tetrahedron,* 29, 3985–3986, 1973.
Stephen et al., *Chem. Abstracts,* 51, 9588, 1957.

*Primary Examiner*—Nicholas S. Rizzo
*Assistant Examiner*—Lisa Jones
*Attorney, Agent, or Firm*—Harry E. Westlake, Jr.; Raymond M. Speer, Jr.

[57] ABSTRACT

Certain novel acyl saccharins and acyl 3-oxo-1,2-benzisothiazolines, their preparation, pharmaceutical compositions and novel methods of inhibiting elatase and treating emphysema are disclosed.

3 Claims, No Drawings

2-(2-FUROYL)1,2-BENZISOTHIAZOLE-3-ONE, 2-(2-FUROYL) SACCHARIN, AND 2-(2-THENOYL) SACCHARIN

BACKGROUND OF THE INVENTION

Elastase is one of the serine proteases, an important family of enzymes within the proteolytic enzyme group whose members are essential to a variety of biological activities, such as digestion, formation and dissolution of blood clots, the immune reaction to foreign cells and organisms and the fertilization of the ovum by the spermatozoon. The proteolytic or protein cutting enzymes are proteins whose function is to alter or decompose other proteins by splitting them into fragments. Elastase acts on bonds in the middle of the protein chain which are adjacent to aliphatic amino acids.

Proteases may be inactivated by inhibitors which block the active site of the enzyme by binding tightly thereto. Naturally occurring protease inhibitors form part of the control or defense mechanisms that are crucial to the well-being of the organism, as the protease enzymes would destroy any protein within reach, including themselves. The naturally occurring enzyme inhibitors have evolved a configuration in the binding region that closely resembles the bound substrate, which is part of the reason they bind to the enzyme so tightly (see Stroud, "A Family of Protein-Cutting Proteins" Sci. Am. July 1974, p. 74-88).

$\alpha_1$-Antitrypsin, a glycoprotein in human serum, has a wide inhibitory spectrum covering trypsin, chymotrypsin, plasmin, kallikrein, elastase, thrombin and a protease from Aspergillus oryzae. The marked reduction in serum $\alpha_1$-antitrypsin has been associated with pulmonary emphysema (see Erickson, S. "Pulmonary emphysema and alpha$_1$-antitrypsin deficiency" Acta. Med. Scand. 1964, 175, 197). Subsequent studies have confirmed and extended this observation (see Morse et al. "A Community Study of the Relation of Alpha$_1$-Antitrypsin Levels to Obstructive Lung Diseases" The New England Journal of Medicine, Vol. 292, No. 6, p. 278, Feb. 6, 1975).

Emphysema has been experimentally induced in laboratory animals by aerosolization into the tracheobronchial tree of the proteolytic enzyme, papain, and more recently by dog polymorphonuclear enriched leukocyte homogenates (see Mass et al. "Induction of Experimental Emphysema" American Review of Respiratory Disease, vol. 106, p. 384, 1972). The pathological changes are similar to and closely resemble human pulmonary emphysema. Also, intratracheally instilled elastase produces marked alterations in lung elastin with dilatation of alveolar ducts and alveoli (see Johanson et al. "Comparison of elastase, collagenase and papain on lung structure and function" Amer. Rev. Resp. Dis. 1971, 103, 908). Papain induced emphysema has been inhibited in the hamster by human $\alpha_1$-antitrypsin (HAAT). Since papain is one of the few proteinases not inhibited by HAAT, the HAAT inhibits the elastase-like enzymes released by polymorphonuclear leukocytes and alveolar macrophages which invade the hamsters' lungs following exposure (see Martorana et al. "Inhibition of Papain-Induced Emphysema in the Hamster by Human Alphal-antitrypsin," Can. J. Physiol. Pharmacol. Vol. 52, No. 3, p. 758-759, 1974 and Kaplan et al. "The induction of emphysema with elastase" Journal of Laboratory and Clinical Medicine, vol. 82, No. 3, 349-356, Sept. 1973). Elastase inhibitors may be used in control of elastase-like enzymes released by polymorphonuclear leukocytes and alveolar macrophages in emphysema.

In rheumatoid arthritis, antigen/antibody complexes have been demonstrated in the synovial fluid and as cytoplasmic inclusions in leukocytes which are chemotactically attracted to the sites of inflammation (see Oronsky et al. "Release of Cartilage Mucopolysaccharide Degrading Neutral Protease from Human Leukocytes", Journal of Experimental Medicine, vol. 138, p. 461-472, 1973). Polymorphonuclear leukocytes (PMN) enter acute inflammatory exudates to phagocytize the immune reactants or microorganisms. During phagocytosis, PMN enzymes are sometimes released extracellularly. When the extracellular release occurs to a degree sufficient to overwhelm the host inhibitors, tissue damage produced by the PMN substances may greatly diminish their beneficial effects. The major portion of neutral proteolytic activity in humans is usually attributed to elastin-like enzymes (see Janoff, "Alanine p-nitrophenyl esterase activity of human leukocyte granules", Biochemical Journal, 114; p. 157-159, 1969). Elastase inhibitors can be used to control PMN mediated tissue damage in acute inflammatory diseases of immunological origin, such as rheumatoid arthritis, caused by elastase.

DETAILED DESCRIPTION OF THE INVENTION

We have found a novel method of inhibiting elastase which comprises the administration of a therapeutically effective amount of a compound of the formula:

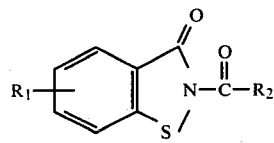

wherein
R$_1$ is halogen, such as fluoro, chloro or bromo, C$_{1-5}$alkoxy, such as methoxy, ethoxy, or propoxy, C$_{1-5}$alkylamino, such as N-methylamino or N-ethylamino, diC$_{1-5}$alkylamino, such as N,N-dimethylamino or N,N-diethylamino, C$_{1-5}$alkoxycarbonyl, such as methoxycarbonyl or ethoxycarbonyl, amino, nitro or especially hydrogen;

R$_2$ is hydrogen, C$_{1-10}$alkyl, such as methyl, ethyl, propyl, butyl, pentyl, hexyl and preferredly branchedC$_{3-10}$alkyl, such as isopropyl, isobutyl, isopentyl, isohexyl, tert-butyl, 2-ethylbutyl, 2-ethylpentyl and especially 2-ethylpropyl, C$_{2-5}$alkenyl, such as allyl, propenyl and especially vinyl, C$_{2-5}$alkynyl, such as ethynyl, 1-propynyl or 2-propynyl, cycloC$_{3-7}$-alkyl, such as cyclobutyl, cyclopentyl, cyclohexyl, cycloheptyl and especially cyclopropyl, halophenyl such as 3-fluorophenyl, 4-fluorophenyl, 2,4-difluorophenyl and especially 2-fluorophenyl, heteroaryl, such as pyrrolyl, pyridyl, pyranyl and especially furyl or thienyl or substituted-heteroaryl, such as sulfo-furyl or N,N-diethylaminomethylfuryl and n is 0 or 2.

In a preferred embodiment, R$_1$ is as defined above, R$_2$ is branchedC$_{3-10}$alkyl, C$_{2-5}$alkenyl, C$_{2-5}$alkynyl, cycloC$_{3-7}$alkyl, fluorophenyl, heteroaryl or substituted-heteroaryl, and n is 0 or 2.

In a more preferred embodiment, $R_1$ is hydrogen, $R_2$ is branched$C_{3-10}$alkyl, $C_{2-5}$alkenyl, cyclo$C_{3-7}$-alkyl, fluorophenyl, furyl, substituted-furyl, thienyl or substituted-thienyl, and n is 0 or 2.

Representative compounds which inhibit elastase, and therefore are useful for treating emphysema and other disorders which may be treated with elastase inhibitors, such as rheumatoid arthritis are the following novel compounds:
2-(2-Furoyl)saccharin;
2-(2-Thenoyl)saccharin;
2-(2-Ethylbutyryl)saccharin;
2-(Cyclopropyanoyl)saccharin;
2-(Acryloyl)saccharin;
2-(2-Fluorobenzoyl)saccharin;
2-(2-Furoyl)-3-oxo-1,2-benzisothiazoline;
2-Acryloyl-3-oxo-1,2-benzisothiazoline;
2-(2-Thenoyl)-3-oxo-1,2-benzisothiazoline;
and the following known compounds
2-(2-Ethylbutyryl-3-oxo-1,2-benzisothiazoline;
2-(Benzoyl)saccharin;
2-(3-Methoxybenzoyl)saccharin.

Another aspect of this invention relates to the novel method of treating emphysema which comprises administering to a patient a therapeutically effective amount of a compound of formula I, supra.

Another aspect of this invention relates to the novel pharmaceutical compositions comprising a non-toxic pharmaceutically acceptable carrier and a compound of formula I, supra.

In a preferred embodiment, the novel pharmaceutical composition comprises a non-toxic pharmaceutically acceptable carrier and a compound of formula II, infra.

The inhibition of elastase and treatment of emphysema in accordance with the method of the present invention is accomplished by orally, rectally, parenterally and especially topically administering to patients the compounds of formula I, supra, or mixtures thereof in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin and acacia. Exemplary of liquid carriers are peanut oil, olive oil, seasame oil and water. Similarly, the carrier or diluent may include a time delay material such as glyceryl monostearate or glyceryl distearate, alone, or with a wax.

Several pharmaceutical forms of the therapeutically useful compositions may be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, a liquid solution, a liquid emulsion or a liquid suspension, and preferrably a liquid which may be sprayed by aerosol or nubulizer. Suppositories may be prepared in the conventional manner by mixing the compounds of this invention with a suitable non-irritating excipient which is solid at room temperature. Exemplary of excipients are cocoa butter and polyethylene glycol. Gels, lotions and aerosol sprays for topical application may be prepared in conventional manners.

The active compounds are administered in a therapeutically effectove amount sufficient to inhibit elastase. The treatment of emphysema is one condition where the inhibition of elastase will arrest the condition, and accordingly the amount of active compound necessary to inhibit elastase is the amount required to treat emphysema. Advantageously, the active compounds will be administered, alone or in a pharmaceutical composition in an amount of from about 1.0 mg to 100 mg per kg body weight per day (50 mg to 5.0 g per patient per day) of the active compound, preferably from about 1.5 mg to 15 mg per kilogram body weight per day. The daily dosage may be given in either single or multiple dosages.

The method of treatment of this invention comprises administering to a patient (animal or human) the compound as previously described admixed with a non-toxic pharmaceutical carrier such as exemplified above. It should be understood that although preferred dosage ranges are given, the dose level for any particular patient depends upon the activity of the specific compound employed. Also many other factors that modify the actions of drugs will be taken into account by those skilled in the art in the therapeutic use of medicinal agents, particularly those described above; for example, body weight, sex, diet, time of administration, route of administration, rate of excretion, drug combination, reaction sensitivities and severity of the particular disease.

The in vitro test exemplified below demonstrates the ability of compounds of formula I, supra, to inhibit elastase. The ability of these elastase-inhibiting compounds to inhibit emphysema is based upon the ability of 2-(2-furoyl)saccharin, a respresentative compound of this invention, to inhibit emphysema by testing for the inhibition of papain-induced emphysema in the test procedure described below (see also Martorana et al. "Inhibition of Papain-Induced Emphysema in the Hamster by Human Alpha$_1$-antitrypsin", supra) and by testing for the inhibition of elastase-induced emphysema in the test procedure described below. In view of the test results, infra, the compounds of formula I, supra, are inhibitors of elastase and may be used to treat emphysema and other disorders which may be treated with elastase inhibitors, such as rheumatoid arthritis. The test procedure described below for papain-induced emphysema in the hamster is representative of recognized procedures used to experimentally papain-induce emphysema in the hamster such as that of Goldring et al. "Sequential Anatomic Changes in Lungs Exposed to Papain and other Proteolytic Enzymes" pages 389–410 in *Pulmonary Emphysema and Proteolysis*, edited by C. Mittman, Academic Press, Inc., New York and London, 1972.

The test procedure described below for elastase-induced emphysema in the hamster is representative of recognized procedures used to experimentally elastase-induce emphysema in the hamster such as that of Kaplan et al., J. Lab. Clin. Med., 82, 349–356, 1973.

Another aspect of this invention is the novel compounds of the formula:

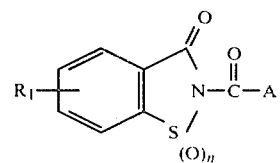

II wherein $R_1$ is halogen, such as fluoro, chloro or bromo, $C_{1-5}$alkoxy, such as methoxy, ethoxy or propoxy, $C_{1-5}$alkylamino, such as N-methylamino or N-ethylamino, di$C_{1-5}$alkylamino, such as N,N-dimethylamino or N,N-diethylamino, $C_{1-5}$alkoxycarbonyl, such as methoxycarbonyl or ethoxycarbonyl, amino, nitro or especially hydrogen;

A is branched$C_{3-10}$alkyl, such as isopropyl, isobutyl, isopentyl, isohexyl, tert-butyl, 2-ethylbutyl, 2-ethylpentyl and especially 2-ethylpropyl, $C_{2-5}$alkenyl, such as allyl, propenyl and especially vinyl, $C_{2-5}$alkynyl, such as ethynyl, 1-propynyl or 2-propynyl, cyclo$C_{3-7}$alkyl, such as cyclobutyl, cyclopentyl, cyclohexyl, cycloheptyl and especially cyclopropyl, fluorophenyl such as 3-fluorophenyl, 4-fluorophenyl, 2,4-difluorophenyl and especially 2-fluorophenyl, heteroaryl, such as pyrrolyl, pyridyl, pyranyl and especially furyl or thienyl or substituted-heteroaryl, such as sulfo-furyl or N,N-diethylaminomethylfuryl and n is 0 or 2, with the proviso that when n is 0, $R_1$ may not be hydrogen or nitro when A is branched$C_{3-10}$alkyl.

In a preferred embodiment:

$R_1$ is hydrogen and A is vinyl, cyclopropyl, fluorophenyl, furyl, substituted-furyl, thienyl or substituted-thienyl when n is 0; and $R_1$ is hydrogen or $C_{1-5}$alkoxycarbonyl and A is branched$C_{3-10}$alkyl, $C_{2-5}$alkenyl, cyclo$C_{3-7}$alkyl, fluorophenyl, furyl, substituted-furyl, thienyl or substituted-thienyl when n is 2.

In a more preferred embodiment:

$R_1$ is hydrogen, A is vinyl, cyclopropyl, furyl, substituted-furyl, thienyl or substituted-thienyl, and n is 0, or $R_1$ is hydrogen, A is branched$C_{3-10}$alkyl or fluorophenyl and n is 2.

Another aspect of this invention is the processes for preparing the novel compounds of formula II, supra, wheren $R_1$ and A are defined above and n is 2, by reacting, preferably by refluxing in a suitable solvent, a compound of the formula:

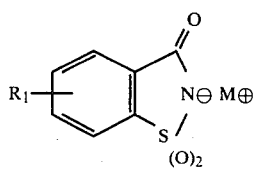
III wherein $M^\oplus$ is an alkali metal or $(NR'_4)^+$ wherein R' is hydrogen or $C_{1-5}$alkyl, with a compound of the formula:

IV wherein

X is chloro, bromo or iodo.

The inert solvent should be dry and may be a hydrocarbon, such as hexane, benzene, toluene or xylene, a $C_{1-5}$alkyl ether such as diethyl ether, a heterocyclic ether such as dioxan and especially tetrahydrofuran (THF), a tertiary amide such as dimethylformamide, dimethylacetamide or hexamethylphosphoramide or a ketone such as acetone, methyl ethyl ketone or mixtures thereof.

The reaction may be carried out at a temperature of from about 0° C. to 250° C., preferably at the reflux temperature of the solvent. The time of reaction is not critical and the reaction is preferably carried out until it is essentially complete. The pressure is not critical and the reaction is generally carried out at atmospheric pressure in an open system. The reaction product may be recovered in the conventional manner, such as by filtration to remove the salt formed, followed by removal of the solvent to recover the product.

The compounds of formula III may be prepared by reacting 3-oxo-1,2-benzisothiazoline 1,1-dioxide (also known as saccharin) with a finely divided metallic alkali metal, such as sodium or potassium. The compounds of formula III may also be prepared by reacting the 3-oxo-1,2-benzisothiazoline 1,1-dioxide with an alkali metal hydride, such as sodium hydride or potassium hydride. The 3-oxo-1,2-benzisothiazoline 1,1-dioxide may also be prepared by reacting a compound of formula V with ammonia followed by oxidation. The various $R_1$ groups may be introduced into the benzene nucleus by methods well known, infra.

Another aspect of this invention is the process for preparing the novel compounds of formula II, supra, wherein $R_1$ and A are as defined above and n is 0, by reacting a compound of the formula:

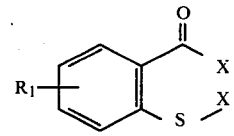
V with a compound of the formula:

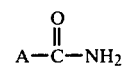
VI wherein X is chloro, bromo or iodo.

The reaction between the compounds of formula V and VI, an intermolecular cyclization, may be carried out in an aprotic solvent which may be a hydrocarbon such as benzene, an ether such as diethyl ether or tetrahydrofuran, an amide such as dimethylformamide or a halogenated hydrocarbon such as methylene chloride, chloroform and especially carbon tetrachloride. The reaction may be carried out in the present of a mild base which may be an alkali metal carbonate such as sodium carbonate, an alkaline earth carbonate such as calcium carbonate, an alkali metal bicarbonate such as sodium bicarbonate, an alkaline earth bicarbonate such as calcium bicarbonate, a tertiary amine such as triethylamine or a pyridine such as pyridine. The mild bases which are liquids at ambient temperatures may also be used in excess as the solvent. The reaction (cyclization) may be carried out between 0° and 150° C., preferably at ambient temperatures. The time of reaction is not critical and the reaction is preferably carried out until it is essentially complete. The pressure is not critical and the reaction (cyclization) is generally carried out at atmospheric pressure in an open system. The acyl 3-oxo-1,2-benzisothiazoline may be recovered in a conventional manner, such as by crystallization and filtration.

The starting material for this process, V, may be prepared by halogenating a compound of the formula:

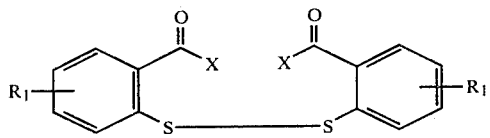

wherein $R_1$ and X are as defined above.

The halogenation may be carried out in an inert solvent which may be selected from a chlorinated hydrocarbon, such as methylene chloride, chloroform and especially carbon tetrachloride or a hydrocarbon, such as benzene. The halogenating agent may be N-chlorosuccinimide, N-bromosuccinimide, an organic hypohalite, such as t-butyl hypochlorite, liquid bromine or preferably gaseous chlorine. The halogenation may be carried out at a temperature of from about 0° C. to 100° C., preferably at ambient temperatures. The time of reaction is not critical and the reaction is preferably carried out until it is essentially complete. The pressure is not critical and the halogenation is generally carried out at atmospheric pressure in an open system. The 2-(chlorocarbonyl)-phenylsulfenyl halide may be recovered in a conventional manner, such as by crystallization and filtration.

The compound of formula VIII may be prepared by treating a bis(2-carboxyphenyl)disulfide with an acid halide forming agent such as a phosphorus trihalide, a phosphorus pentahalide, a phosphorus oxytrihalide, phosgene and preferably a thionyl halide (especially thionyl chloride) by itself or in an inert solvent. The inert solvent may be a hydrocarbon such as toluene, xylene and especially benzene. The mixture is refluxed with stirring until it is essentially complete.

The bis(2-carboxyphenyl)disulfide may be prepared from o-aminobenzoic acid (also known as anthranilic acid) by diazotization, reaction with an alkali metal $C_{1-5}$alkyl xanthate (such as sodium ethyl xanthate) and oxidation with air or a mild peroxide solution. The bis(2-carboxyphenyl)disulfide may also be prepared from o-chlorobenzoic acid by reaction with sodium disulfide. The various $R_1$ groups may be introduced into the benzene nucleus of the o-aminobenzoic acid or the o-chlorobenzoic acid by methods well known, infra.

Compounds of formula II, supra, wherein $R_1$ and A are as defined above and n is O, may also be prepared by cyclizing a compound of the formula:

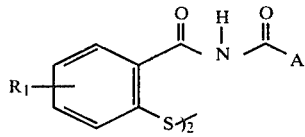

wherein A and $R_1$ are as defined above, with an excess of a halogenating agent. The halogenation is carried out under conditions similar to the halogenation used to produce the compounds of formula V, supra.

The starting material of this process, VII, may be prepared by reacting 2 moles of an amide, VI, supra, with 1 mole of a compound of formula VIII, supra.

The starting materials employed in the foregoing methods have been described in the literature and many are commercially available, except where described below. The various $R_1$ groups may be introduced into the benzene ring in by well known methods, such as nitration for the nitro group; reduction of the nitro group with either hydrogen and a catalyst, such as Raney nickel, finely divided platinum or palladium or with finely divided tin and hydrochloric acid; reductive alkylation with a $C_{1-5}$alkylaldehyde to produce a $C_{1-5}$alkylamino or di$C_{1-5}$alkylamino by conducting the hydrogenation in the presence of a $C_{1-5}$alkylaldehyde; or diazotization of the amino group followed by reaction with (a) water, sulfuric acid and heat (95° C.) to produce the hydroxyl group; (b) potassium iodide and heat (95° C.) to produce the iodo group; (c) cuprous chloride to produce the chloro group; (d) cuprous cyanide and potassium cyanide to produce the cyano group; (e) hydrobromic acid and powdered metallic copper to produce the bromo group; (f) powdered copper or zinc and benzene to produce the phenyl group; (g) sodium arsenite to produce the arsonate group; (h) potassium mercaptide to produce the mercapto group; (i) thioglycolic acid to produce the carboxymethylthio group; or (j) sodium azide to produce the azide group. The 3-oxo-1,2-benzisothiazolines may be converted to the corresponding 3-oxo-1,2-benzisothiazolines 1,1-dioxides (also known as saccharins) by oxidation with an appropriate oxidizing agent such as hydrogen peroxide ($H_2O_2$) or potassium permanganate ($KMnO_4$).

The following examples are given to illustrate the invention and are not intended to limit it in any manner. All parts are given in parts by weight unless otherwise expressed.

EXAMPLE 1

4-Sulfo-2-furoyl chloride

4-Sulfo-2-furoic acid (0.1 mole) is stirred with 30 ml of thionyl chloride ($SOCl_2$) for 40 minutes at 60° C. The reaction mixture is evaporated to dryness to give 4-sulfo-2-furoyl chloride.

EXAMPLE 2

5-(N,N-Diethylaminomethyl)-2-furoyl chloride

A. Ethyl 5-(N,N-diethylaminomethyl)-2-furoate

Ethyl 5-(chloromethyl)-2-furoate (0.1 mole) is refluxed with diethylamine (0.25 mole) in 40 ml of benzene for one hour. The benzene solution is filtered off and washed with water. The organic layer is separated and dried over magnesium sulfate. The magnesium sulfate is removed by filtration and the organics are evaporated to dryness. The residue is distilled to give a pure fraction of ethyl 5-(N,N-diethylaminomethyl)-2-furoate boiling at 97°–106° C. at 0.1 mm of Hg.

B. 5-(N,N-Diethylaminomethyl)-2-furoyl chloride

The ethyl 5-(N,N-diethylaminomethyl)-2-furoate from 2A, above, (0.1 mole) in 50:50 aqueous alcoholic 10% sodium hydroxide is refluxed for 20 minutes, cooled and the alcohol evaporated off. The aqueous layer is extracted with ethyl acetate and then brought to a pH of 7.0 with 0.1 N sulfuric acid. The aqueous solution is evaporated to dryness and the powder is refluxed in 60 ml of thionyl chloride ($SOCl_2$) for four hours. The reaction mixture is evaporated to dryness and the acid chloride.hydrochloride is extracted with 1:1 ethyl acetate:isopropanol. The ethyl acetate solution is evaporated to yield 5-(N,N-diethylaminomethyl)-2-furoyl chloride.hydrochloride.

EXAMPLE 3

2-(2-Furoyl)-3-oxo-1,2-benzisothiazoline-6-carboxylic acid methyl ester, 1,1-dioxide

A. 3-Oxo-1,2-benzisothiazoline-6-carboxylic acid methyl ester

A solution of 19.5 g (0.1 mole) of 3-oxo-1,2-benzisothiazoline-6-carboxylic acid in 40 ml of isopropanol is treated with an excess of a solution of diazomethane in ether added at 0° C. with stirring over a period of 10 minutes. The reaction mixture is evaporated to dryness and the 3-oxo-1,2-benzisothiazoline-6-carboxylic acid methyl ester is obtained as an oil.

B. 3-Oxo-1,2-benzisothiazoline-6-carboxylic acid methyl ester, 1,1-dioxide

3-Oxo-1,2-benzisothiazoline-6-carboxylic acid methyl ester, from example 3A, above, is dissolved in ethyl acetate and 2 equivalents of aqueous 3% by volume hydrogen peroxide is added. The organic layer is separated and dried and 3-oxo-1,2-benzisothiazoline-6-carboxylic acid methyl ester, 1,1-dioxide is isolated by evaporation of the solvent.

C. 3-Oxo-1,2-benzisothiazoline-6-carboxylic acid methyl ester, 1,1-dioxide, sodium salt 3-Oxo-1,2-benzisothiazoline-6-carboxylic acid methyl ester, 1,1-dioxide, from example 3B, above, (0.1 mole) is dissolved in 40 ml of benzene and 3.5 g (0.15 mole) of metalic sodium is added over one hour with cooling. 3-Oxo-1,2-benzisothiazoline-6-carboxylic acid methyl ester, 1,1-dioxide, sodium salt is filtered off and dried.

D. 2-(2-Furoyl)-3-oxo-1,2-benzisothiazoline-6-carboxylic acid methyl ester, 1,1-dioxide A mixture of 2-furoyl chloride (0.1 mole) and 3-oxo-1,2-benzisothiazoline-6-carboxylic acid methyl ester, 1,1-dioxide, sodium salt, from example 3C, above, is refluxed in 100 ml of tetrahydrofuran for 3 hours. The reaction mixture is filtered hot and the filtrate is concentrated to give the product. The product is triturated with ether and air dried to give 2-(2-furoyl)-3-oxo-1,2-benzisothiazoline-6-carboxylic acid methyl ester, 1,1-dioxide.

Similarly, when an equivalent amount of 2-thenoyl chloride, 3-methoxybenzoyl chloride, benzoyl chloride, pivaloyl chloride, 2-ethylbutyryl chloride, acryloyl chloride, cyclopropylcarbonyl chloride, 2-fluorobenzoyl chloride, 4-sulfo-2-furoyl chloride or 5-(N,N-diethylaminomethyl)-2-furoyl chloride is substituted for the 2-furoyl chloride in the above example, there is obtained 2-(2-thenoyl)-3-oxo-1,2-benzisothiazoline-6-carboxylic acid methyl ester, 1,1-dioxide, 2-(3-methoxybenzoyl)-3-oxo-1,2-benzisothiazoline-6-carboxylic acid methyl ester, 1,1-dioxide, 2-benzoyl-3-oxo-1,2-benzisothiazoline-6-carboxylic acid methyl ester, 1,1-dioxide, 2-pivaloyl-3-oxo-1,2-benzisothiazoline-6-carboxylic acid methyl ester, 1,1-dioxide, 2-(2-ethylbutyryl)-3-oxo-1,2-benzisothiazoline-6-carboxylic acid methyl ester, 1,1-dioxide, 2-acryloyl-3-oxo-1,2-benzisothiazoline-6-carboxylic acid methyl ester, 1,1-dioxide, 2-cyclopropylcarbonyl-3-oxo-1,2-benzisothiazoline-6-carboxylic acid methyl ester, 1,1-dioxide, 2-(2-fluorobenzoyl)-3-oxo-1,2-benzisothiazoline-6-carboxylic acid methyl ester, 1,1-dioxide, 2-(4-sulfo-2-furoyl)-3-oxo-1,2-benzisothiazoline-6-carboxylic acid methyl ester, 1,1-dioxide or 2-[5-N,N-diethylaminomethyl)-2-furoyl]-3-oxo-1,2-benzisothiazoline-6-carboxylic acid methyl ester, 1,1-dioxide.

EXAMPLE 4

2-Fluorobenzoyl)-saccharin

A. 2-Fluorobenzoyl chloride

A mixture of 14.0 g (0.1 mole) of 2-fluorobenzoic acid and 30 ml of thionyl chloride ($SOCl_2$) is refluxed in 70 ml of benzene for four hours. The mixture is cooled and concentrated under vacuum to give 2-fluorobenzoyl chloride as a liquid.

Similarly, when an equivalent amount of 2-carboxythiophene, 3-methoxybenzoic acid or benzoic acid is substituted for the 2-fluorobenzoic acid in the above example, there is obtained 2-chlorocarbonylthiophene (also known as 2-thenoyl chloride), 3-methoxybenzoyl chloride or benzoyl chloride.

B. 2-(2-Fluorobenzoyl)-saccharin

A mixture of 2-fluorobenzoyl chloride, from example 4A, above, and 18.5 g (0.09 mole) of sodium saccharin is refluxed in 100 ml of tetrahydrofuran (THF) overnight. The reaction mixture is filtered hot, and the filtrate is concentrated to a partial solid/oil. The product is triturated with ether and air dried to yield 10.3 g of 2-(2-fluorobenzoyl)saccharin, m.p. 148°-151° C.

Similarly, when an equivalent amount of 2-thenoyl chloride, 3-methoxybenzoyl chloride, benzoyl chloride, pivaloyl chloride, 2-ethylbutyryl chloride, acryloyl chloride, cyclopropylcarbonyl chloride, 2-furoyl chloride, 4-sulfo-2-furoyl chloride or 5-(N,N-diethylaminomethyl)-2-furoyl chloride is substituted for 2-fluorobenzoyl chloride in the above example, there is obtained 2-(2-thenoyl)saccharin (m.p. 127°-131° C.), 2-(3-methoxybenzoyl)saccharin (m.p. 129°-131° C.), 2-(benzoyl)-saccharin (m.p. 156°-159° C.), 2-(pivaloyl)-saccharin (m.p. 209°-210° C.), 2-(2-ethylbutyryl)saccharin (m.p. 82°-83° C.), 2-(acryloyl)saccharin (m.p. 177°-180° C.), 2-(cyclopropylcarbonyl)saccharin (m.p. 203°-205° C.), 2-(2-furoyl)saccharin (m.p. 133°-135° C.), 2-(4-sulfo-2-furoyl)saccharin (m.p. 220°-223° C.) or 2-[5-(N,N-diethylaminomethyl)-2-furoyl]saccharin.

EXAMPLE 5

5-(N,N-Diethylaminomethyl)-2-furamide

A mixture of 25.3 g (0.1 mole) of n-butyl 5-(N,N-diethylaminomethyl)-2-furoate is added to 50 ml of liquid ammonia in a pressure vessel. The mixture is held at 180° C. and 2000 pounds per square inch gage pressure for 8 hours. The mixture is cooled to ambient temperature and evaporated to dryness giving 5-(N,N-diethylaminomethyl)-2-furamide (m.p. 164°-165° C.).

EXAMPLE 6

2-(2-Furoyl)-3-oxo-1,2-benzisothiazoline

A. Bis(2-chlorocarbonylphenyl)disulfide

A solution of 30.6 g (0.1 mole of bis(2carboxyphenyl)-disulfide in 200 ml of benzene is treated with 16 ml (0.22 mole) of thionyl chloride ($SOCl_2$) and refluxed with stirring for 16 hours. The mixture is filtered and the filtrate is concentrated under vacuum to a pale yellow solid. After trituration in hexane, the solid is filtered to give bis(2-chlorocarbonylphenyl)disulfide, m.p. 145°-148° C.

B. 2-(2-Furoyl)-3-oxo-1,2-benzisothiazoline

5 G (0.015 mole) of bis(2-chlorocarbonylphenyl)disulfide is suspended in 500 ml of carbon tetrachloride (CCl₄) and treated with chlorine gas until all solids are dissolved (about 0.5 hours). The solution is then concentrated under vacuum and the residue is taken up in 45 ml of carbon tetrachloride (CCl₄). 3.0 G (0.027 mole) of 2-furoylamide in 50 ml of benzene is added to the solution. The solution is aged 10 minutes, concentrated under vacuum and the residue is quenched in 75 ml of 2.5 N hydrochloric acid. The precipitate is isolated and washed well with water to yield 2.5 g of 2-(2-furoyl)-3-oxo-1,2-benzisothiazoline m.p. 157°–161° C. The 2-(2-furoyl)-3-oxo-1,2-benzisothiazoline is recrystallized from toluene, washed with hexane, and dried giving a m.p. of 160°–161° C.

Similarly, when an equivalent amount of acrylamide, 2-thenoylamide, pivaloylamide, 2-ethylbutyrylamide, 2-ethylhexanoylamide or 5-(N,N-diethylaminomethyl)-2-furamide is substituted for the 2-furoylamide in the above example there is obtained 2-acryloyl-3-oxo-1,2-benzisothiazoline, 2-(2-thenoyl)-3-oxo-1,2-benzisothiazoline, 2-pivaloyl-3-oxo-1,2-benzisothiazoline, 2-(2-ethylbutyryl)-3-oxo-1,2-benzisothiazoline (m.p. 56°–58° C.), 2-(2-ethylhexanoyl)-3-oxo-1,2-benzisothiazoline or 2-[5-(N,N-diethylaminomethyl)-2-furoyl]-3-oxo-1,2-benzisothiazoline.

EXAMPLE 7

A suspension of 2-(2-furoyl)-saccharin having a particle size distribution of 90% below 10 microns suitable for use as an inhalation aerosol and having the following composition is as follows:

| per 200 doses | per 70 mg dose |
|---|---|
| 2.0 g 2-(2-furoyl)-saccharin | 10 mg |
| 530 mg Freon 11 | 2.65 mg |
| q.s. ad 14 g Freons 12/114 (80–20 mixture) | 57.35 mg |

Step A—Particle Sizing

The particle size of the 2-(2-furoyl)-saccharin is reduced by glass bead milling of a concentrate in Freon 11 as follows:
(1) To a dry, clean, plastic coated 250 ml glass vial with a 20 mm neck opening add about 100 g of dry, clean, 6 mm pyrex glass beads. Add 20 g of dry 2-(2-furoyl)-saccharin and 5.3 g of Freon 11. Seal using a polyethylene-lined pressure cap.
(2) Roller mill for 24 hours or until the particle size of the 2-(2-furoyl)-saccharin is below 10 microns measured by microscopic examination.

Step B—Preparation of Aerosols

The 14 g aerosol bottles are cold filled as follows:
(1) Chill concentrate and Freons 12/114 (80–20 mixture) using dry ice and acetone.
(2) Fill 2.530 g of chilled concentrate and 11.47 g of Freons 12/114 (80–20 mixture) into chilled clear plastic coated 10 ml glass vials and seal with a VCA Drain All Valve.

Each spray will deliver a metered dose of 70 mg containing 10 mg of 2-(2-furoyl)-saccharin.

EXAMPLE 8

A suspension of 2-(2-furoyl)-saccharin for inhalation administration at a particle size distribution of 90% less than 10 microns in an aerosol form and having a composition similar to Example 7 but containing 20–50 mg per dose is prepared by increasing the quantities of 2-(2-furoyl)-saccharin, Freon 11 proportionate to the increase in 2-(2-furoyl)-saccharin and increasing the size of the valve metering device.

EXAMPLE 9

A suspension of 2-(2-furoyl)-saccharin for inhalation administration at a particle size distribution of 90% less than 10 microns in an aerosol form and having compositions similar to Examples 7 and 8 but containing anhydrous ethanol, is prepared by replacing or adding to the Freon 11, in amounts of 0.1 g to 2 g per 14 g aerosol container. The anhydrous ethanol is used as a vehicle for the bead milling, lubricant for the suspension's passage through the metered valve and a deflocculating agent.

EXAMPLE 10

Example 10 is similar to Example 9 except in addition to or in the absence of the Freon 11 and ethanol, 0.1 g to 2 g of propylene glycol, oleyl alcohol, hexylene glycol, Dowanol DPM, triacetin, ethyl lactate, ethyl acetate or Freon 113 may be used for the same reasons as noted in Example 9.

EXAMPLE 11

A suspension of 2-(2-furoyl)-saccharin having a particle size destribution of 90% below 10 microns suitable for use as an inhalation aerosol propelled with nitrogen and having the following composition is as follows:

| per 200 doses | |
|---|---|
| 2.0 g 2-(2-furoyl)-saccharin | 10 mg |
| 2.0 g ethanol anhydrous | 10 mg |
| q.d. ad Liquid Nitrogen | 50 mg |

This example is prepared the same as Example 7 except the quantity of the 2-(2-furoyl)-saccharin is glass bead milled in an anhydrous ethanol vehicle and liquid nitrogen is used as the propellant. The VCA Drain All Valve is replaced with Emson nitrogen propellant metering valve.

EXAMPLE 12

A suspension of 2-(2-furoyl)-saccharin for inhalation administration at a particle size distribution of 90% less than 10 microns in a nitrogen propelled aerosol form having a composition similar to Example 11 but containing 20–200 mg per dose is prepared by increasing the quantities of 2-(2-furoyl)-saccharin, anhydrous ethanol necessary to bead mill the drug and increasing the size of the valve metering device.

EXAMPLE 13

A suspension of 2-(2-furoyl)-saccharin for inhalation administration as an aqueous or hydroalcoholic or alcoholic or glycolic suspension containing the drug at a particle size distribution of 90% less that 10 microns for use with a DeVilbiss type atomizer or nebulizer is as follows:

|  |  | per dose |
|---|---|---|
| (A) | 2-(2-furoyl)-saccharin | 10-200 mg |
|  | Water | q.s. |
|  | Preservative | q.s. |
| (B) | 2-(2-furoyl)-saccharin | 10-200 mg |
|  | Ethanol 95% | q.s. |
| (C) | 2-(2-furoyl)-saccharin | 10-200 mg |
|  | Water | q.s. |
|  | Propylene Glycol | q.s. |
| (D) | 2-(2-furoyl)-saccharin | 10-200 mg |
|  | Ethanol 95% | q.s. |
|  | Water | q.s. |
| (E) | 2-(2-furoyl)-saccharin | 10-200 mg |
|  | Ethanol 95% | q.s. |
|  | Propylene Glycol | q.s. |

The particle size of the 2-(2-furoyl)-saccharin is reduced by glass bead (6 mm) milling in the vehicle and the composition is adjusted to the desired volume with additional vehicle (A) to (E).

An appropriate wetting agent such as polysorbate 80 0.1-4 mg/ml may be added to (A) through (E).

EXAMPLE 14

A powder for inhalation having a particle size 90% below 10 microns for use in a dispensing device such as a Spinhaler ® Turbo-inhaler having a composition as follows:

|  |  | per dose |
|---|---|---|
| (A) | 2-(2-furoyl)-saccharin | 10 |
|  | (90% less than 10 microns) | 10-250 mg |
| (B) | 2-(2-furoyl)-saccharin |  |
|  | (90% less than 10 microns) | 10-100 mg |
|  | Mannitol (microatomized) | 190-100 mg |

These powders are made to the appropriate particle size by air attrition or mechanical million.

EXAMPLE 15

To 3.0 ml of 0.2 mM of N-t-Butoxycarbonylalanyl-alanyl-prolyl-alanyl-p-nitroanilide(BOC-AAPAN) in a cuvette is added 0.01 to 0.1 ml of dimethylsulfoxide (DMSO). After mixing, a measurement is taken at 410 mu to detect any spontaneous hydrolysis due to the presence of the test compound. 0.1 ml of elastase (0.8 $\mu$g/ml) is then added and the change in optical density per minute ($\Delta$OD/min) at 410 mu is measured and recorded using a Gilford 240 spectrophotometer.

| Compound | ID$_{40}$ ($\mu$g/ml) for Elastase |
|---|---|
| 2-(2-Ethylbutyryl)-3-oxo 1,2-benzisothiazoline | 0.2 |
| 2-(2-Furoyl)-3-oxo-1,2-benzisothiazoline | 0.2 |
| 2-(2-Furoyl)-saccharin | 0.2 |
| 2-(2-Ethylbutyryl)saccharin | 0.2 |
| 2-(Cyclopropylcarbonyl)saccharin | 2.5 |
| 2-Acryloyl saccharin | 0.5 |
| p-(t-Butyl)phenyl furoate | 40 |

ID$_{50}$ Dose level at which 50% inhibition is observed.

EXAMPLE 16

Papain-Induced Emphysema in the Hamster

Male Syrian hamsters in the weight range of 70-90 g were used. Food and water was allowed ad libitum except in the exposure chamber. The animals were anesthetized with pentobarbital 60 mg/kg intraperitoneally (i.p.) and saline (control) or 2-(2-furoyl)-saccharin suspended in distilled water in doses of 0.3, 1 and 3 mg was given intratracheally (i.tr.) through a slightly bent capillary tube (Kimax-51 No. 34500). A 5 cm piece of polyethylene tubing (Intramedic PE 205) fixed to the distal end of the capillary tube was immersed in an ampoul containing 0.2 ml of the suspension and the inspiratory efforts of the animal resulted in the inhalation of the liquid material in a few seconds. Approximately 40 minutes later the animals were exposed to an aerosol of distilled water or 3% papain (Matheson, Coleman and Bell) for 3 hours. The aerosol was generated by two nebulizers (De Vilbiss 40) attached to the sides of a 28 liter chamber and operated at a pressure of 10 lbs. p.s.i. During this period 80-100 ml of solution was used.

Seven days after the exposure the animals were sacrificed with an overdose of pentobarbital, exanguinated by cutting the renal arteries and the lungs were excised, weighed and placed in a cylindrical 0.45 liter plethysmograph with the trachea tied to a conducting tube. The latter was connected to a respiratory pump (E & M Inst. Co., Houston, Tex.) modified to provide static inflation and deflation of the lungs. Transpulmonary pressure was recorded on the abcissa of a Honeywell 530 x-y recorder through a Grass volumetric pressure transducer (PT 5A). Changes in lung volume were recorded on the ordinate of a spirometer (10 ml capacity) connected to a Harvard linear motion transducer.

The specific static compliance (SSC) of the lungs was determined as follows: the lungs were inflated to a pressure of 20 cm H$_2$O and then deflated at 30 second intervals by steps of 5 cm H$_2$O pressure. The procedure was repeated and the second pressure volume defation curve was used for analysis. SSC was then calculated according to the formula $\Delta V/\Delta P \times W$, where $\Delta V$ represents change in lung volume (ml) following change in pressure ($\Delta P$) from 5 to 0 cm H$_2$O, and W is the lung wet weight (g).

Subsequently, the lungs were degassed and fixed intratracheally with formalin at a constant pressure of 15 cm H$_2$O for at least 48 hours and then dehydrated at the same pressure. All lungs were cleared in toluene, embedded under vacuum in parafin and each pair was blocked together. Two laterosagittal sections (6$\mu$) of each lung were made and stained with hematoxylin and eosin and the extent of emphysematous lesions was quantitatively estimated by measuring the average intra-alveolar distance (mean linear intercept of Lm). A total of 20 random histologic fields were evaluated both vertically and horizontally and subsequently corrected for distortion and shrinkage. The internal surface area of the lungs measured at post-fixation lung volume (V) and corrected to an arbitrary total lung volume of 3 ml (ISA$_3$) was calculated according to the formula 4V/Lm. In all studies statistical evaluation consisted of analysis of variance and significance was taken at $P \leq 0.05$.

Results of the physiological and histological tests obtained for all groups of animals are entered below. As can be seen, 2-(2-furoyl)-saccharin prevented the development of the emphysematous lestions as evaluated by both physiologic and histologic methods. Inhibition was dose related but significant only for doses of 1 and 3 mg of 2-(2-furoyl)-saccharin i.tr., maximal effect being observed with the later dose (74, 84 and 65 percent inhibition of changes in SSC, Lm and ISA$_3$, respectively).

| Group | Number of Animals | Physiology S.S.C. $\Delta V/\Delta P \times W$ Mean ± S.E. | % Inhibition |
|---|---|---|---|
| (A) Saline i.tr. + water aerosol | 5 | 0.252 ± 0.020* | — |
| (B) Saline i.tr. + papain aerosol | 12 | 0.672 ± 0.042 | — |
| (C) 2-(2-furoyl)-saccharin 0.3 mg i.tr. + papain aerosol | 10 | 0.529 ± 0.041 | 34 |
| (D) 2-(2-furoyl)-saccharin 1 gm i.tr. + papain aerosol | 10 | 0.471 ± 0.039* | 48 |
| (E) 2-(2-furoyl)-saccharin 3 mg i.tr. + papain aerosol | 7 | 0.360 ± 0.017* | 74 |

*$P<0.05$ versus saline i.tr. + papain aerosol group

| Group | Histology Lm, μ Mean ± S.E. | % inhibition | $I.S.A._3 cm^2$ Mean ± S.E. | % inhibition |
|---|---|---|---|---|
| A | 80.32 ± 2.63* | — | 1600 ± 58* | — |
| B | 106.39 ± 3.60 | — | 1155 ± 29 | — |
| C | 88.44 ± 2.54* | 69 | 400 + 38* | 58 |
| D | 90.87 ± 2.40* | 59 | 1344 ± 34* | 42 |
| E | 84.39 ± 2.68* | 84 | 1445 ± 54* | 65 |

*$p<0.05$ versus saline i.tr. + papain aerosol group

EXAMPLE 17

Elastase-Induced Emphysema in the Hamster

Male Syrian hamsters in the weight range of 70–90 g were used. Porcine pancreatic elastase (Worthington Biochemical Corp., N.J.) was used for the induction of emphysema. A dose of 0.1 ml suspended in 0.2 ml of distilled water was administered i.tr. to pentobarbital sodium (60 mg/kg i.p.) anesthetized animals. 2-(2-Furoyl)saccharin was added to the elastase suspension approximately 5–10 minutes prior to i.tr. administration. Animals receiving elastase suspension alone served as emphysematous controls and another group receiving 0.2 ml of saline served as untreated controls. Seven days later, the animals were sacrificed and the extent of emphysematous lesions in the lungs was quantitatively estimated by the measurement of the Lm as described above.

In all studies statistical evaluation consisted of analysis of variance and significance was taken at $P \leq 0.05$.

Results of histological changes observed in all groups of animals are reported in Table 2. As can be seen, addition of 0.03 to 0.3 mg of 2-(2-furoyl)saccharin to elastase prior to its i.tr. administration exhibited a partial but statistically significant protective effect, while 1 mg of 2-(2-furoyl)-saccharin completely prevented the development of pulmonary emphysematous lesions.

| Group | Number of Animals | Lm(μ) Mean ± S.E. | ΔLm(μ) | % inhibition of ΔLm |
|---|---|---|---|---|
| Saline i.tr. | 6 | 79.72 ± 2.43* | — | — |
| Elastase 0.1 mg i.tr. | 6 | 113.03 ± 6.74* | +33 | — |
| Elastase 0.1 mg + 2-(2-furoyl)-saccharin 0.03 mg i.tr. | 4 | 96.61 ± 3.22* | +17 | 48 |
| Elastase 0.1 mg + 2-(2-furoyl)-saccharin 0.1 mg i.tr. | 5 | 94.34 ± 4.31* | +15 | 54 |
| Elastase 0.1 mg + 2-(2-furoyl)-saccharin 0.3 mg i.tr. | 5 | 96.27 ± 2.36* | +16 | 51 |
| Elastase 0.1 mg + 2-(2-furoyl)-saccharin 1.0 mg i.tr. | 5 | 77.68 ± 2.54* | −2 | 100 |

*$P<0.05$ versus elastase 0.1 mg i.tr. group

What is claimed is:
1. 2-(2-Furoyl)-1,2-benzoisothiazoline-3-one.
2. 2-(2-Furoyl)saccharin.
3. 2-(2-Thenoyl)saccharin.

* * * * *